(12) United States Patent
Jia et al.

(10) Patent No.: US 11,618,025 B2
(45) Date of Patent: Apr. 4, 2023

(54) APPARATUS AND METHOD FOR ON-CHIP MICROFLUIDS DISPENSING

(71) Applicant: University of Macau, Macau (CN)

(72) Inventors: Yanwei Jia, Macau (CN); Haoran Li, Macau (CN); Ren Shen, Macau (CN); Cheng Dong, Macau (CN); Tianlan Chen, Macau (CN); Jie Gao, Macau (CN); Pui-ln Mak, Macau (CN); Rui Paulo da Silva Martins, Macau (CN)

(73) Assignee: University of Macau, Macau (CN)

( * ) Notice: Subject to any disclaimer, the term of this patent is extended or adjusted under 35 U.S.C. 154(b) by 484 days.

(21) Appl. No.: 16/648,009

(22) PCT Filed: Aug. 1, 2018

(86) PCT No.: PCT/CN2018/097847
§ 371 (c)(1),
(2) Date: Mar. 17, 2020

(87) PCT Pub. No.: WO2020/024119
PCT Pub. Date: Feb. 6, 2020

(65) Prior Publication Data
US 2020/0254457 A1    Aug. 13, 2020

(51) Int. Cl.
*B01L 3/00* (2006.01)
*G01N 33/53* (2006.01)

(52) U.S. Cl.
CPC ........ *B01L 3/502792* (2013.01); *G01N 33/53* (2013.01); *B01L 2300/0645* (2013.01); *B01L 2300/161* (2013.01); *B01L 2400/0427* (2013.01)

(58) Field of Classification Search
None
See application file for complete search history.

(56) References Cited

FOREIGN PATENT DOCUMENTS

WO    WO-2009086403 A2 * 7/2009 .......... B01F 13/0071

OTHER PUBLICATIONS

Suh et al; A Review on Mixing in Microfluidics; Micromachines 2010, 1, 82-111; doi:10.3390/mi1030082.
Lee et al.; Microfluidic Mixing: A Review; International Journal of Molecular Sciences, 2011, 12, 3263-3287; doi:10.3390/ijms12053263.

(Continued)

*Primary Examiner* — J. Christopher Ball
(74) *Attorney, Agent, or Firm* — S&F/WEHRW

(57) ABSTRACT

Provided is an apparatus, system and method for on-chip microfluids dispensing. The apparatus comprising a substrate; a plurality of first electrodes arranged one next to another on the substrate; a dielectric layer above and enclosing the plurality of first electrodes; and a second electrode on the substrate, wherein each of the plurality of first electrodes is in electric communication with a respective first driving signal input; wherein the second electrode is in electric communication with a second driving signal input; wherein the plurality of first electrodes define a continuous fluid path along a longitudinal direction for retaining microfluids, and wherein the second electrode is arranged within the continuous fluid path and defines a jetting position and an adjacent mixing position within the continuous fluid path.

21 Claims, 6 Drawing Sheets

(56) References Cited

OTHER PUBLICATIONS

Coelho et al.; A Digital Microfluidics Platform for Loop-Mediated Isothermal Amplification Detection; Sensors, 2017, 17, 2616; doi:10.3390/s17112616.
Shih et al.; A Feedback Control System for High-Fidelity Digital Microfluidics; Lab on a Chip, 2011, 11, 535-540; DOI: 10.1039/c0lc00223b.
Hadwen et al.; Programmable large area digital microfluidic array with integrated droplet sensing for bioassays—ESI; Lab on a Chip, 2012, 12, 3305-3313.
Vallet et al.; Limiting phenomena for the spreading of water on polymer films by electrowetting; The European Physical Journal B; 1999, 11, 583-591.

\* cited by examiner

APPARATUS AND METHOD FOR ON-CHIP MICROFLUIDS DISPENSING

CROSS-REFERENCE TO RELATED APPLICATIONS

This application is the National Stage of International Application No. PCT/CN2018/097847, filed Aug. 1, 2018.

TECHNICAL FIELD

The present disclosure generally relates to a lab-on-a-chip apparatus and methods of use thereof, and more particularly to an apparatus, system and method for on-chip microfluids dispensing in a microfluidic system.

BACKGROUND ART

Traditional biochemical experiments use micropipettes to dispense specific volumes of a substance. Typical micropipettes can accurately dispense volumes from 0.1 µL to over 1,000 µL. The accurate dispensation of volumes smaller than 0.1 µL is highly challenging if not impossible. The accuracy and precision of both collecting and dispensing the desired volume, especially at values approaching 0.1 µL, present further challenges. The accuracy and precision are subject to a number of variables, such as the quality of micropipettes, the viscosity of the dispensed substance, the calibration and maintenance, as well as the laboratory practice.

Lab-on-a-chip (LOC) systems have attracted commercial and academic attention over the years as a substitute for traditional volumetric pipettes. LOC technology can reduce the scale of single and/or multiple lab processes down to a chip format. LOC systems exhibit additional advantages, such as low fluid volume consumption, faster analysis and response time and better process control.

As the scale goes down, the microfluidic sample manipulation in LOC apparatuses becomes more challenging. Dispensing and mixing of two or more microfluids with high precision is particularly challenging. Different chip designs have been developed for on-chip microfluidic sample dispensing and mixing.

Channel-based microfluidic platforms, where a continuous microfluidic flow is forced through micro-scale channels with external forces like air pressure have been developed to accurately measure and dispense microfluids. These systems are disadvantaged by the need of bulky and complex external devices.

Electronic-based digital microfluidic (DMF) platforms have also been developed, where microfluidic droplets are provided on an array of electrodes and driven by an electro-wetting on dielectric (EWOD) force. Mixing of two or more microfluids in DMF platforms is typically achieved by driving two microfluidic droplets to merge. The merged droplet may then be moved on several electrodes repeatedly to improve the mixing. Due to the limit of the electrodes, the two microfluidic droplets have to be generally equal in volume. As a result, the merged droplet typically has double the volume and the reagent(s) in the two microfluidic droplets will be diluted by half, which can complicate and/or limit application of this system. The increase of volume also makes the manipulation of the merged droplet more difficult.

A need therefore exists for a novel LOC apparatus that eliminates or diminishes at least one or more of the disadvantages and problems described above.

DISCLOSURE OF INVENTION

Provided herein is a method for on-chip microfluids dispensing, comprising the steps of: (a) providing a plurality of first electrodes underlying a continuous fluid path for retaining microfluidic drops, the plurality of first electrodes are capable of generating an electro-wetting on dielectric (EWOD) force acting on the microfluidic drops and along the continuous fluid path; (b) providing a second electrode embedded within one or more of the plurality of first electrodes, the second electrode defines a jetting position on the continuous fluid path; (c) providing a first microfluidic drop at the jetting position; (d) applying a second driving signal via the second electrode to the first microfluidic drop, such that a controlled volume of the first microfluidic drop is jetted to a mixing position next to the jetting position on the continuous fluid path; and (e) providing a second microfluidic drop at the mixing position, such that the second microfluidic drop absorbs the controlled volume of the first microfluidic drop jetted to the mixing position.

In certain embodiments, step (c) comprises loading the first microfluidic drop at a first loading position away from the jetting position and applying a first driving signal to the plurality of first electrodes to generate a EWOD force that drives the first microfluidic drop from the first loading position to the jetting position.

In certain embodiments, step (e) comprises loading the second microfluidic drop at a second loading position away from the mixing position and applying a first driving signal to the plurality of first electrodes to generate a EWOD force that drives the second microfluidic drop from the second loading position to the mixing position.

In certain embodiments, step (e) further comprises applying a first driving signal to the plurality of first electrodes to generate a EWOD force that drives the second microfluidic drop back and forth along the continuous fluid path at the mixing position.

In certain embodiments, the first driving signal is an AC signal with a peak to peak voltage of 5 to 300 V and a frequency of 1-4 kHz.

In certain embodiments, the second driving signal is an AC signal with a peak to peak voltage of 500 to 2,000 V and a frequency of 10 Hz to 2 kHz.

In certain embodiments, the peak pulse signal is applied for 0.1 to 10 seconds for each jetting operation.

In certain embodiments, the jetted volume of the first microfluidic drop is positively correlated to at least one of the following factors: the voltage of the second driving signal, the frequency of the second driving signal, the duration of the second driving signal and the width of the second electrode.

In certain embodiments, the method is used for dispensing DNA solutions, protein solutions, organic solutions or inorganic salt solutions.

In certain embodiments, the jetted volume of the first microfluidic drop is in the range of $10^{-15}$ to $10^{-6}$ liters.

Provided herein is an apparatus for on-chip microfluids dispensing, the apparatus comprises a bottom plate, the bottom plate comprises a substrate; a plurality of first electrodes arranged one next to another on the substrate; a dielectric layer above and enclosing the plurality of first electrodes; and a second electrode on the substrate, wherein each of the plurality of first electrodes is in electric communication with a respective first driving signal input; wherein the second electrode is in electric communication with a second driving signal input; wherein the plurality of first electrodes define a continuous fluid path along a longitudinal direction for retaining microfluidic drops, and wherein the second electrode is arranged within the continuous fluid path and defines a jetting position and an adjacent mixing position within the continuous fluid path.

In certain embodiments, the second electrode has a width between 10 μm and 500 μm.

In certain embodiments, the second electrode is embedded within one or more adjacent first electrodes.

In certain embodiments, the one or more adjacent first electrodes comprise an elongate channel across the one or more adjacent first electrodes in the longitudinal direction, and the second electrode is arranged within the elongate channel.

In certain embodiments, the second electrode is stacked on one or more adjacent first electrodes and encapsulated by the dielectric layer.

In certain embodiments, the apparatus further comprises a hydrophobic layer on top of the dielectric layer.

In certain embodiments, the apparatus further comprises a plurality of fences on the plurality of first electrodes to prevent microfluidic drops from drifting away from the continuous fluid path.

In certain embodiments, the apparatus further comprises a top plate; and a spacer between the top plate and the bottom plate, wherein the top plate, the bottom plate and the spacer define a cavity for retaining microfluidic drops.

In certain embodiments, the top plate comprises a conductive and grounded layer.

In certain embodiments, the apparatus comprises multiple independent continuous fluid paths. Provided herein is a system for on-chip microfluids dispensing, the system comprises an apparatus according to the previous aspects of the present disclosure, and a control unit, the control unit comprises an array of relays having a plurality of first driving signal outputs and a second driving signal output, each of the plurality of the first driving signal outputs is in electric communication with a respective first driving signal input of the apparatus, and the second driving signal output is in electric communication with the second driving signal input of the apparatus; a signal generator in electric communication with the array of relays, the signal generator generates a first driving signal and a second driving signal; and a controller in electric communication with the array of relays, the controller determines the outputs of the plurality of first driving signal outputs and the second driving signal output.

These and other aspects, features and advantages of the present disclosure will become more fully apparent from the following brief description of the drawings, the drawings, the detailed description of certain embodiments and appended claims.

BRIEF DESCRIPTION OF DRAWINGS

The appended drawings contain figures of certain embodiments to further illustrate and clarify the above and other aspects, advantages and features of the present invention. It will be appreciated that these drawings depict embodiments of the invention and are not intended to limit its scope. The invention will be described and explained with additional specificity and detail through the use of the accompanying drawings in which.

MODES FOR CARRYING OUT THE INVENTION

Figure 1:
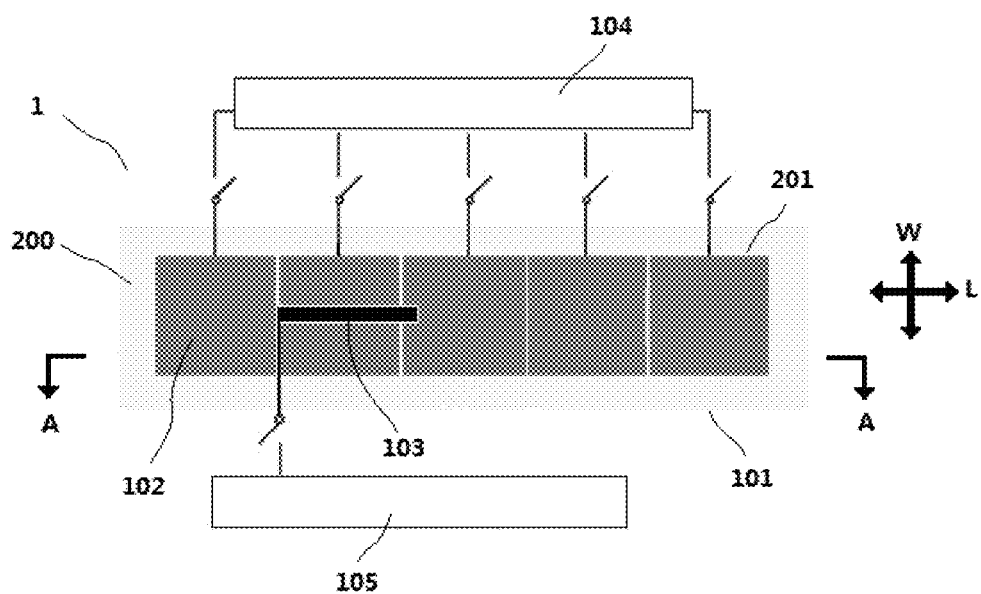
FIG. 1 is a top view of an apparatus for on-chip microfluids dispensing according to certain embodiments of the present disclosure.
Figure 2:
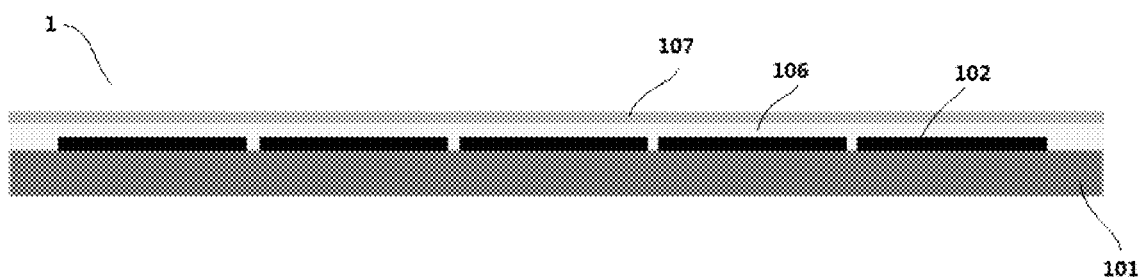
FIG. 2 is a cross-section view of the apparatus for on-chip microfluids dispensing according to certain embodiments of the present disclosure, taken along A-A in FIG. 1.

FIG. 1 shows a top view of an apparatus 1 for on-chip microfluids dispensing according to certain embodiments of the present disclosure. The apparatus 1 can be any digital microfluidic device, such as a microchip for drug delivery or discovery, a microchip for cellular analysis or engineering, or a microchip for diagnostic sensing. Alternatively, the apparatus 1 can be a portion of any microfluidic device or system. As shown in FIG. 1, the apparatus 1 comprises a substrate 101. The substrate 101 can be made from insulator ($\rho > 10^8$ Ω-cm) or semi-conductor ($10^{-3}$ Ω-cm$<\rho<10^8$ Ω-cm) materials, such as silicon, glass, ceramics and polymers, for instance polydimethylsiloxane (PDMS), thermoset polyester, thermoplastic polymers, polystyrene, polycarbonate, poly-methyl methacrylate (PMMA), poly-ethylene glycol diacrylate (PEGDA) and polyurethane. FIG. 2 is a cross-section view of the apparatus 1 taken along A-A in FIG. 1. A plurality of first electrodes 102 are arranged on the substrate 101. The plurality of first electrodes 102 can be made from any conductor ($\rho < 10^{-3}$ ω-cm) material, such as metals, alloys, conductive ink or conductive polymer, for instance silver (Ag), copper (Cu), Aluminum (Al), Platinum (Pt), chromium (Cr), Tungsten (Wu), or Indium tin oxide (ITO). The plurality of first electrodes 102 can be formed by conventional methods, such as etching, photolithography or deposition. A dielectric layer 106 is disposed above the plurality of first electrodes 102 to enclose and seal the plurality of first electrodes 102. The dielectric layer 106 prevents any direct contact between the microfluids and the plurality of first electrodes 102, thus minimizing any erosion of the electrodes from contact with the microfluids and/or any contamination of the microfluids from contact with the plurality of first electrodes, and allowing a much higher electric field (i.e. stronger electro-wetting effect) to be applied to the microfluids. The dielectric layer 106 can be made from any dielectric material that can be made into a thin membrane, such as SU8 photoresist, Parylene C, plastic wrap, PDMS, PMMA, PI, cover slide glass etc. The dielectric layer 106 can be formed by conventional methods, such as deposition. In certain embodiments, the dielectric layer 106 has a thickness from 2 μm to 100 μm, but other ranges of thickness are also possible, so long as the dielectric layer 106 does not break down at the applied driving voltage. In certain embodiments, there is a further hydrophobic layer 107 on top of the dielectric layer 106. The hydrophobic layer 107 is meant to reduce the contact angle hysteresis and therefore facilitate the movement of microfluids thereon. The hydrophobic layer 107 can be made from any hydrophobic materials, such as Teflon® and Cytop®. The plurality of first electrodes 102 together with the dielectric layer 106 and the hydrophobic layer 107 on top of it define a holding area 200 on the substrate 101 for retaining microfluids.

While FIG. 1 shows the holding area 200 has a rectangular contour, it is not intended by the present disclosure to impose any restriction on the contour of the holding area 200. For instance, the holding area 200 can have a square, circular, ring-shaped, L-shaped, X-shaped contour or any other suitable contour. The holding area 200 can cover substantially the entire surface area of the substrate 101, or only part of the surface area of the substrate 101. There can be more than one holding area 200 on one substrate 101, such that multiple dispensing operations can be conducted concurrently on one substrate 101. For instance, two, three, four, five, six, seven, eight, nine, ten or more separate holding area 200 can be provided on one substrate 101.

The plurality of first electrodes 102 are arranged one next to another on the substrate 101 along a longitudinal direction L, forming a planar electrode array. The planar electrode array defines a continuous fluid path 201 for the microfluids within the holding area 200. The plurality of first electrodes 102 are disposed under the continuous fluid path 201. In certain embodiments, the continuous fluid path 201 covers essentially the same area as the holding area 200. In other embodiments, the continuous fluid path 201 covers an area smaller than that of the holding area 200. Where there are multiple holding areas 200, there will equally be multiple independent continuous fluid paths 201 for concurrent dispensing operations. Depending on the arrangement of the plurality of first electrodes 102, the continuous path 201 can be straight or curved, linear or non-linear. In FIG. 1, each first electrode 102 is represented as a square block, without limitation to its actual contour and configuration. The first electrode 102 can have regular or irregular contour which can be optimized for microfluidic drop manipulation. In certain embodiments, the first electrode 102 can have a rectangular, square or oval contour. Alternatively, the first electrode 102 can have a zig-zag or finger-like contour. Each first electrode 102 can have a dimension in the range between 50 µm to 3000 µm, between 100 µm to 2000 µm, between 400 µm to 1000 µm, or between 600 µm to 800 µm. The plurality of first electrodes 102 are electrically isolated from each other. Each of the plurality of first electrodes 102 is connected to a first driving signal input 104, such that the plurality of first electrodes 102 can be activated individually by a respective first driving signal. As the plurality of the first electrodes 102 are activated in a predetermined manner, an electro-wetting on dielectric (EWOD) force can be generated and applied to the microfluidic drops on the continuous fluid path 201. The microfluidic drops can be driven by the EWOD force to move along the continuous fluid path 201. More specifically, a microfluidic drop can be forced to move from one location above a first electrode 102 to another location above another first electrode 102, as will be discussed in more details below.

Figure 5:
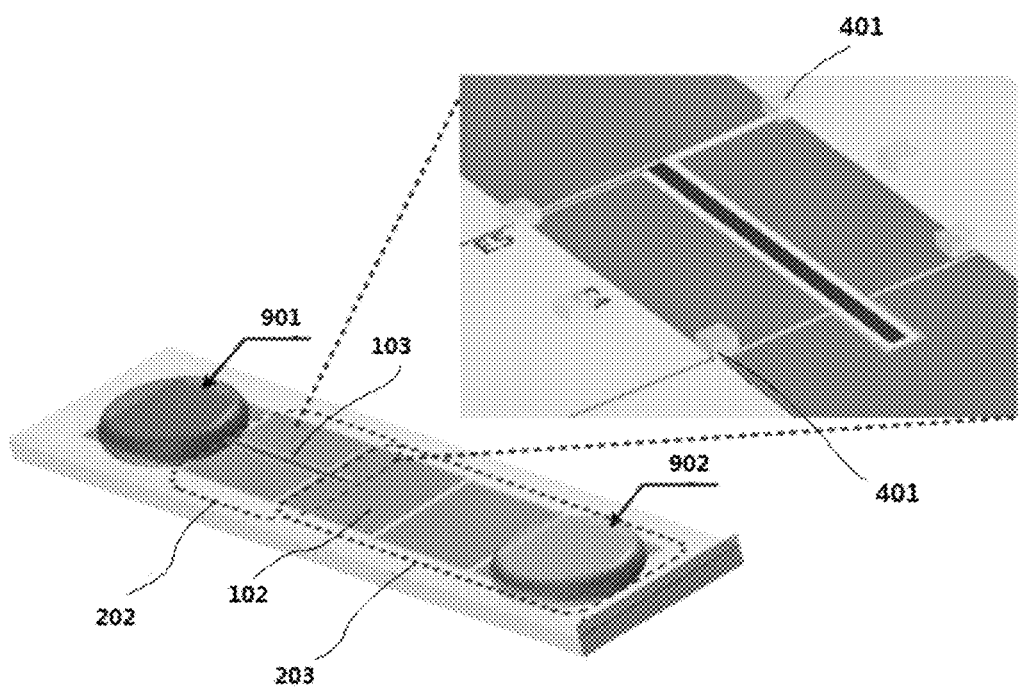
FIG. 5 is a perspective view of the apparatus for on-chip microfluids dispensing according to certain embodiments of the present disclosure.

Also provided on the substrate and within the continuous fluid path 201, is a second electrode 103. In certain embodiments, the apparatus 1 can comprise multiple second electrodes 103. For instance, the apparatus 1 can comprise two, three, four, five, six, seven, eight, nine, ten or more second electrodes 103 at different locations of the continuous fluid path 201. In FIG. 1, the second electrode 103 is represented as an elongate bar, without limitation to its actual shape and configuration. In certain embodiments, the second electrode 103 has an elongate bar shape as shown in FIG. 5, with a width of 10 µm to 500 µm, particularly 20 µm to 400 µm, 40 µm to 300 µm, 60 µm to 200 µm, 70 µm to 100 µm, or 80 µm to 90 µm. The width of the second electrode 103 will affect the contour of the contact between the microfluidic drop and the second electrode 103, which in turn will affect the jetting volume of the microfluidic drop on the second electrode 103. In certain embodiments, the second electrode 103 is embodied within one or more (e.g. two or three) of the plurality of first electrodes 102 and electrically isolated from the one or more of the plurality of first electrodes 102. For instance, an elongate area extending across one or more adjacent first electrodes 102 in the longitudinal direction L can be etched away or otherwise removed from the one or more adjacent first electrodes 102, resulting an elongate channel across the one or more adjacent first electrodes 102 in the longitudinal direction L. The second electrode 103 having an elongate bar configuration can then be provided along the elongate channel. In certain embodiments, the second electrode 103 can be stacked on one or more adjacent first electrodes 102. The second electrode 103 can be encapsulated by the dielectric layer 106 and/or the hydrophobic layer 107. In certain embodiments, the second electrode 103 is disposed at the center of the one or more adjacent first electrodes 102 with respect to the traverse direction W of the apparatus 1. The second electrode 103 is connected to a second driving signal input 105, and can be activated by a second driving signal.

Figure 3:
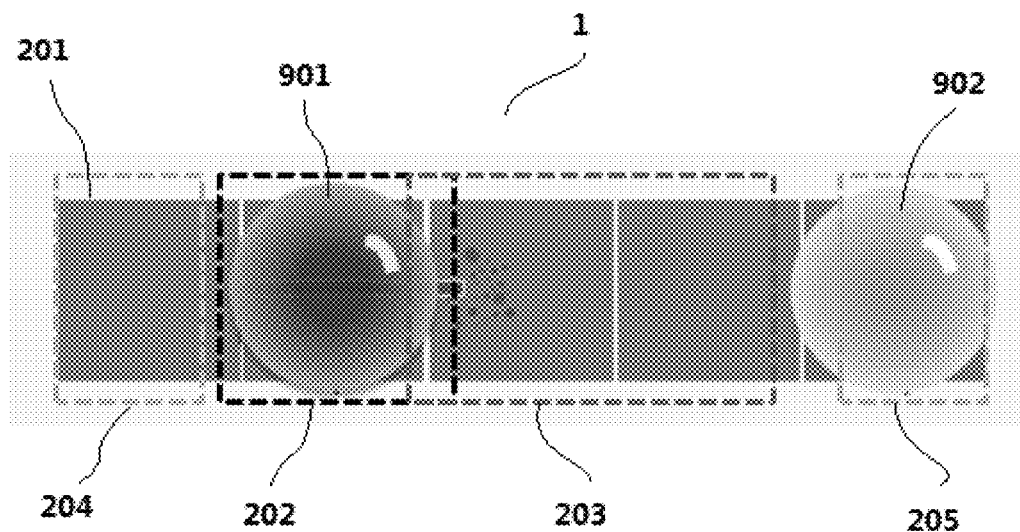
FIG. 3 is a schematic drawing of a continuous fluid path on the apparatus for on-chip microfluids dispensing according to certain embodiments of the present disclosure.

As shown in FIG. 3, the second electrode 103 defines a jetting position 202 on the continuous fluid path 201. As will be discussed in more detail below, when a first microfluidic drop 901 comprising an reagent at a known concentration is loaded at the jetting position 202 of the continuous fluid path 201 and the second electrode 103 is activated in a predetermined manner, the first microfluidic drop 901 will vibrate in an electrical field generated by the second electrode 103 and lose its stability. As a result, a controllable volume of the first microfluidic drop 901 can be jetted out of the first microfluidic drop and to a mixing position 203 that is next to the jetting position 202 and within the continuous fluid path 201. The jetting position 202 may to some extent overlap with the mixing position 203 as shown in FIG. 3. When a second microfluidic drop 902 is then loaded at the mixing position 203 of the continuous fluid path 201, the volume of the first microfluidic drop 901 jetted onto the mixing position 203 can be absorbed by the second microfluidic drop 902. As a result, a precise volume of the first microfluidic drop 901 comprising the reagent at the known concentration is mixed with the second microfluidic drop 902.

In certain embodiments, the continuous fluid path 201 further comprises a first loading position 204 away from the jetting position 202 for loading the first microfluidic drop 901, and a second loading position 205 away from the mixing position 203 for loading the second microfluidic drop 902. Once loaded at the first loading position 204, the first microfluidic drop 901 can be moved by the EWOD force generated by the activation of the plurality of first electrodes 102 in a predetermined manner to the jetting position 202; and the second microfluidic drop 903, once loaded at the second loading position 205, can be moved by the EWOD force generated by the activation of the plurality of first electrodes 102 in a predetermined manner to the mixing position 203.

It is not intended by the present disclosure to limit the number of jetting positions 202, mixing positions 203 and/or loading positions 204, 205, and/or their arrangements within the holding area 200. However, a jetting position 202 generally has a mixing position 203 next to it. As will be apparent to a skilled person having the benefit of the present disclosure, when more than two (e.g. three or four) microfluidic drops are intended to be dispensed or mixed in a controllable manner, it can be achieved with a single jetting position 202 and a single mixing position 203, or with multiple jetting positions 202 and multiple mixing positions 203. The loading positions 204, 205 can be present, but are not absolutely necessary.

Figure 4:
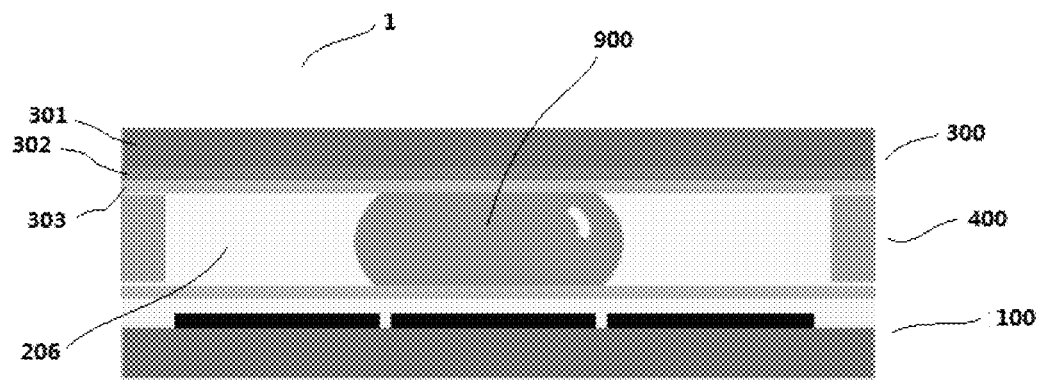
FIG. 4 is a cross-section view of the apparatus for on-chip microfluids dispensing according to some further embodiments of the present disclosure.

FIG. 4 shows some further embodiments of the apparatus 1. The apparatus 1 comprises a bottom plate 100 comprising the substrate 101, the plurality of first electrodes 102, the one or more second electrodes 103, the dielectric layer 104 and the hydrophobic layer 105 as discussed above; a top plate 300 and a spacer 400 therebetween.

The top plate 300 is not absolutely necessary. However, the existence of the top plate 300 will affect the strength of electric field generated by the plurality of first electrodes 102 or by the second electrode 103. In certain embodiments, the top plate 300 is conductive and grounded, which limits the electric field between the top plate 300 and the bottom plate 100 and thereby boosts up the electric field strength. As a result, a lower voltage is required for microfluidic drop transportation and ejection. In certain embodiments, the second electrode 103 can be provided on or in the top plate 300.

The spacer 400 can be made from any materials that are robust enough to separate the top plate 300 and the bottom plate 100. The spacer 400 can be provided at the edge of the bottom plate 100. The spacer 400 can be a frame around the bottom plate 100 or comprise a plurality of posts. The thickness of the spacer 400 can range from 5 μm to 500 μm, 10 μm to 400 μm, 20 μm to 300 μm, 50 μm to 200 μm, or 80 μm to 150 μm. In certain embodiments, the ratio between the dimension of the first electrode 102 and the thickness of the spacer 400 can be between 5 to 10, between 6 to 9, or between 7 to 8.

The bottom plate 100, the top plate 300 and the spacer 400 together define a cavity 206 for retaining microfluidic drops 900 as shown in FIG. 4. In certain embodiments, a plurality of block-shape fences 401 are arranged at the corners of each first electrode 102, as shown in FIG. 5. The fences 401 help to prevent microfluidic drops from drifting away from the continuous fluid path 201 when no EWOD force is applied.

The top plate 300 comprises a substrate 301 that is similar to the substrate 101 of the bottom plate 100. The substrate 301 can be coated with an indium tin oxide (ITO) layer 302 for the top plate 300 to be conductive and grounded. Likewise, the top plate 300 can comprise a hydrophobic layer 303 to facilitate movement of microfluidic drops within the cavity 206.

Figure 6:
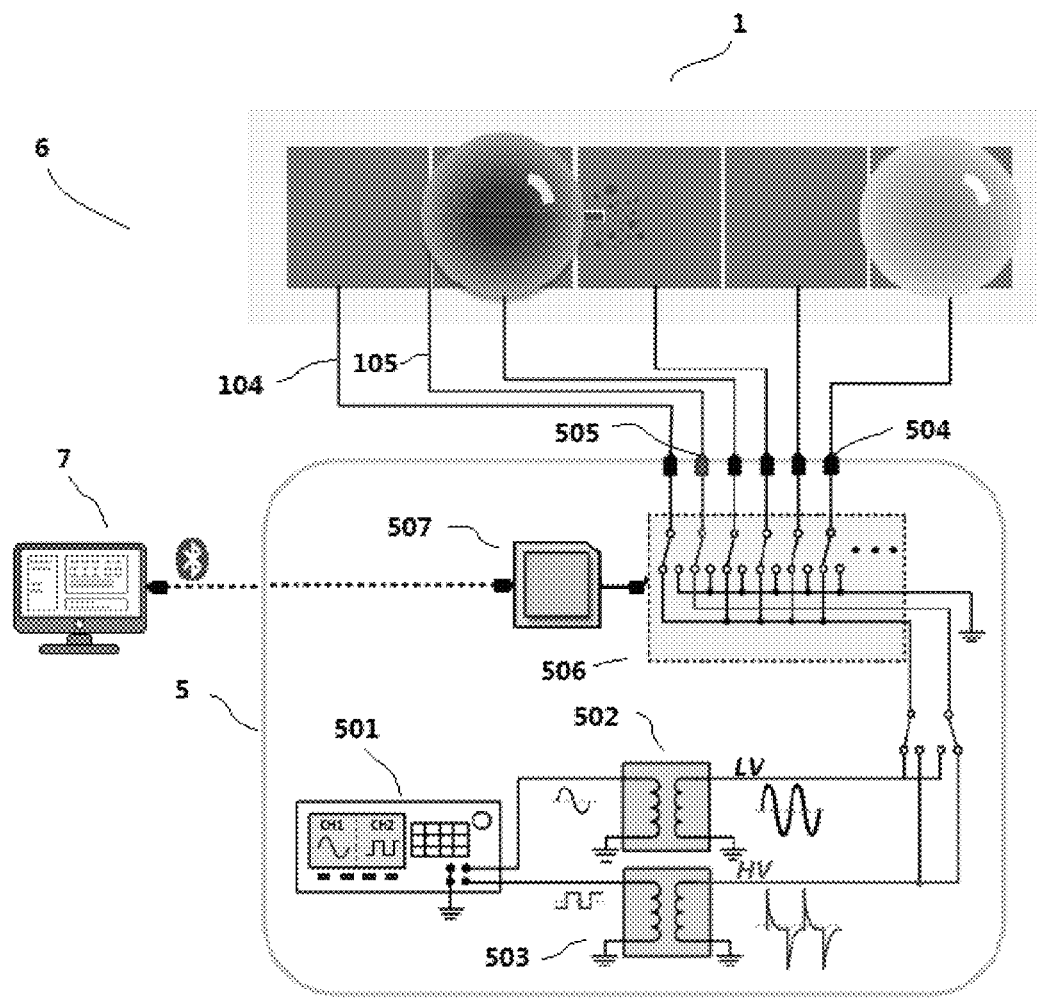
FIG. 6 is a schematic drawing of a system for on-chip microfluids dispensing according to certain embodiments of the present disclosure.
Figure 7:
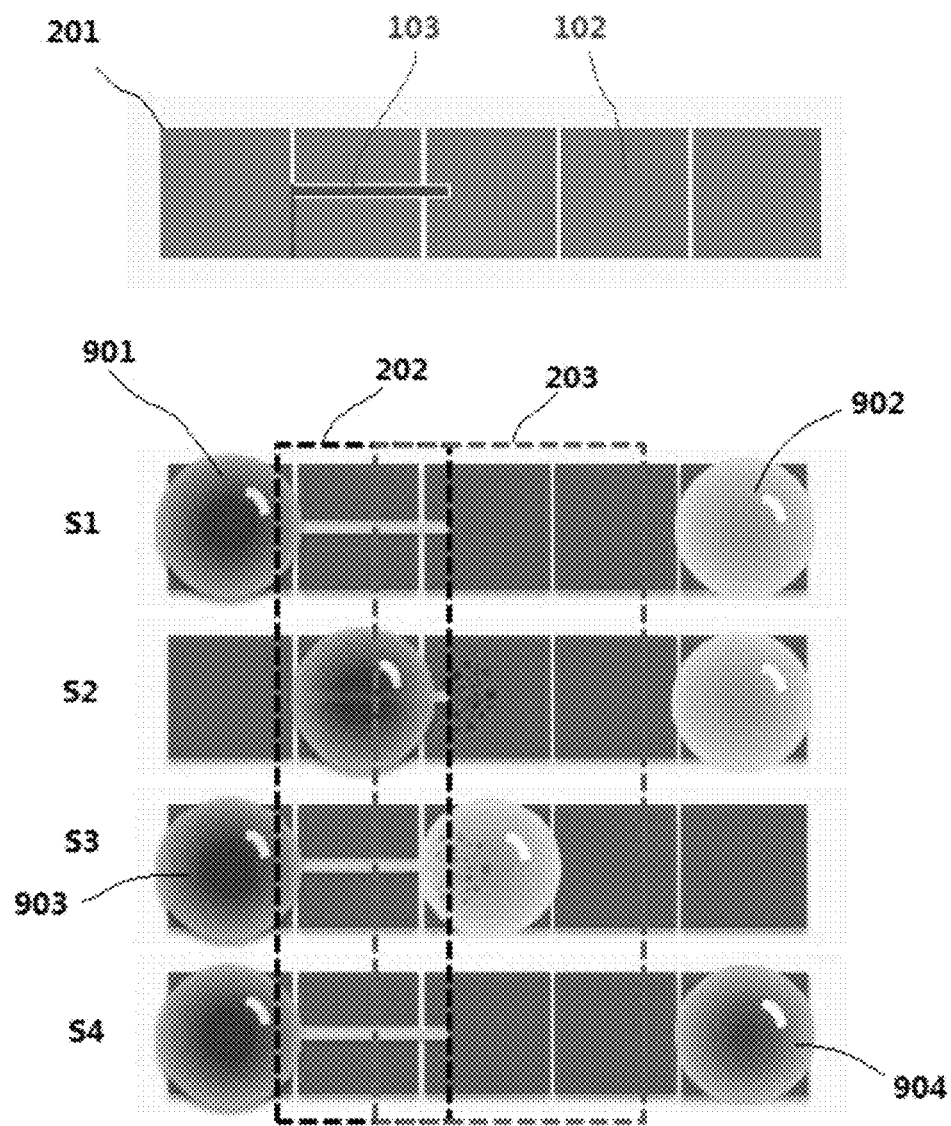
FIG. 7 is a schematic drawing of a method for on-chip microfluids dispensing according to certain embodiments of the present disclosure.

The present disclosure further discloses a system 6 for on-chip microfluids dispensing. As shown in FIG. 6, the system 6 comprises the apparatus 1 discussed above and a control unit 5 in electrical communication with the apparatus 1. The control unit 5 comprises an array of relays 506, the relays 506 provide a plurality of first driving signal outputs 504 that are in electrical communication with the plurality of first driving signal inputs 104 of the apparatus 1, and one or more second driving signal outputs 505 that are in electrical communication with the one or more second driving signal inputs 105 of the apparatus 1. The array of relays 506 receives a first driving signal LV and a second driving signal HV from an AC signal generator 501. In certain embodiments, a first transformer 502 is provided to amplify the first driving signal LV generated by the AC signal generator 501 and a second transformer 503 is provided to amplify the second driving signal HV generated by the AC signal generator 501. A controller 507 is electrically connected with the array of relays 506 to control the array of relays 506, and consequently to control how the plurality of first electrodes 102 and one or more second electrodes 103 of the apparatus 1 are activated. Depending on the control algorithm of the controller 507, the plurality of first driving signal outputs 504 can output the first driving signal LV or a ground signal at a given time, and the one or more second driving signal outputs 505 can output the second driving signal HV or a ground signal at a given time. In certain embodiments, the controller 507 is electrically connected to the AC signal generator 501 such that the first driving signal LV and/or the second driving signal HV (e.g. their waveform, magnitude, frequency and duty ratio) can be varied as desired. The controller 507 can be any computing device, such as a circuit board, PAL, GAL, CPLD, FPGA and ASIC. In certain embodiments, the controller 507 is in communication with an external device 7, such as a personal computer, a hand held device or a pad, to receive a user input to exercise manual control of the outputs of the first driving signal LV and the second driving signal HV. The communication between the controller 507 and the external device 7 can be wired or wireless, such as by cable, Wi-Fi, Bluetooth, IrDA, ZigBee, NFC, UWB and DECT. Further disclosed herein is a method for on-chip microfluids dispensing. The method can be practiced with the apparatus 1 and system 6 of the present disclosure or any other similar apparatus or system. The method can be used, for example, to dispense DNA solutions; protein solutions; organic solutions, such as IPA or alcohol; or aqueous chemical solutions, such as inorganic salt solutions. As shown in FIG. 7, a continuous fluid path 201 is provided allowing microfluidic drops to move along the path under a EWOD force generated by a plurality of first electrodes 102 underlying the continuous fluid path 201. The EWOD force can drive microfluidic drops on the continuous fluid path 201 to move along the continuous fluid path 201. There is a jetting position 202 provided on the continuous fluid path 201, where a second electrode 103 is disposed to stimulate a jetting operation of a microfluidic drop resting at the jetting position 202. The jetting operation ejects a controlled volume of the first microfluidic drop onto a mixing position 203 next to the jetting position 202 on the continuous fluid path 201. As shown in step S1 of FIG. 7, a first microfluidic drop 901 comprising a reagent of a known concentration is loaded onto a first loading position 204, and a second microfluidic drop 902 of a known volume is loaded onto a second loading position 205. The first microfluidic drop 901 is then driven by a EWOD force generated by the plurality of first electrodes 102 along the continuous fluid path 201 from the first loading position 204 to the jetting position 202. The EWOD force is generated by activating the plurality of first electrodes 102 with a first driving signal in a pre-determined manner. The first microfluidic drop 901 can be driven from a location above a first electrode 102 to another location above the next first electrode 102 by activating the next first electrode 102 with the first driving signal LV. In other words, the plurality of first electrodes 102 starting from the first loading position 204 to the jetting position 202 are activated sequentially with the first driving signal LV, so that the first microfluidic drop 901 can be driven by the EWOD force from the first loading position 204 to the jetting position 202. In certain embodiments, the first driving signal LV can be an AC signal having a magnitude (peak-to-peak voltage) between 5-300V and a frequency of 1-4 kHz. For instance, the magnitude of the first driving signal LV can be between 10-200V, between 20-180V, between 40-160V, or between 60-120V. The frequency of the first driving signal LV can be between 1.5-3.5 kHz, between 2-3 kHz, or between 2.3-2.7 kHz. In certain embodiments, the first driving signal. LV is a sin wave signal or a pulse wave signal. Other waveforms or parameters of the first driving signal LV are also possible so long as the signal does not induce ejection phenomenon of the microfluidic drop. The first driving signal LV is applied to a first electrode 102 for a duration sufficient for the microfluidic drop 901 to move thereto. A person skilled in the art having the benefit of the present disclosure will be able to determine a suitable waveform, magnitude and frequency of the first driving signal, the duration of the first driving signal based on the relevant factors, such as the properties and thickness of the dielectric layer, the hydrophobicity of the contact surface, the properties of the microfluids and the medium surrounding the microfluids (e.g. air or oil).

After the first microfluidic drop 901 is moved to the jetting position 202, the second electrode 103 is activated by a second driving signal HV such that the first microfluidic drop 901 undergoes vibration and ejects a controlled volume out of it to a mixing position 203, as shown in step S2. The volume of the first microfluidic drop 901 is jetted in the form of many tiny droplets. To ensure the tiny droplets are jetted within the continuous fluid path 201, it is preferred that the second electrode 103 is disposed at the center of the continuous fluid path 201 with respect to the transverse (width) direction. In certain embodiments, the second driving signal HV can be a peak pulse AC signal having a magnitude (peak-to-peak voltage) between 500-2,000V, a frequency of 10 Hz-2 kHz and a duty ratio of 5%-50%. For instance, the magnitude of the second driving signal HV can be between 550-1,800V, between 600-1,600V, between 650-1,400V or between 700-1,200V. The frequency of the second driving signal HV can be between 20 Hz-1.8 kHz, between 50 Hz-1.6 kHz, between 80 Hz-1.4 kHz, between 100 Hz-1.2 kHz, between 200 Hz-1.0 kHz, between 400 Hz-800 Hz, or between 500 Hz-700 Hz. One or more jetting operations may be performed at one time. For each jetting operation, the second driving signal HV can be applied to the second electrode 103 for a duration of 0.1 to 10 seconds, for example 0.2 to 9 seconds, 0.3 to 8 seconds, 0.4 to 7 seconds, 0.5 to 6 seconds, 0.6 to 5 seconds, 0.7 to 4 seconds, 0.8 to 3 seconds, or 0.9 to 2 seconds. A longer duration of the second driving signal HV means a larger volume ejected from the microfluidic drop.

After the jetting operation, the remaining portion of the first microfluidic drop less the jetted volume 903 keeps intact and is moved away from the jetting position 202 by the EWOD force generated in the same manner as described above. The remaining portion of the first microfluidic drop 903 may be returned to the first loading position 204 or some other location on the continuous fluid path 201 for use in the next cycle or other purposes. The second microfluidic drop 902 of a known volume can then be moved to the mixing position 203, as shown in step S3. Like for the first microfluidic drop 901, the second microfluidic drop 902 can be moved along the continuous fluid path 201 by a EWOD force generated by activating the plurality of first electrodes 102 from the second loading position 205 to the mixing position 203 with a first driving signal LV in a predetermined manner. While the second microfluidic drop 902 is being moved to the mixing position 203 and passes by the controlled volume of the first microfluidic drop 901 that is jetted onto the mixing position 203, the second microfluidic drop 902 absorbs the controlled volume of the first microfluidic drop 901. As a result, a precise mixing of a controlled volume of the first microfluid comprising a reagent of a known concentration and the second microfluid of a known volume is achieved. As the jetted volume of the first microfluid may be in the form of many tiny droplets, the second microfluidic drop 902 can be driven to move back and forth along the continuous fluid path 201 at the mixing position 203 to improve the absorption and mixing. Advantageously, the back and forth movement of the second microfluidic drop 902 can enable the jetted volume of the first microfluidic drop 901 to be absorbed by the second microfluidic drop 902 as much as possible. Having absorbed the jetted volume of the first microfluidic drop 901, the second microfluidic drop 904 can be returned to the second loading position 205 or some other location for further processing by a EWOD force, as shown in step S4.

In certain embodiments, the first and second microfluidic drops 901, 902 can be directly loaded onto the jetting position 202 and the mixing position 203 respectively. In other embodiments, a first microfluidic drop 901 may be extracted by the EWOD force from a fluid reservoir (not shown) in fluid communication with the continuous fluid path 201, and driven along the continuous fluid path 201 to the jetting position 202. Likewise, a second microfluidic drop 902 can be extracted by the EWOD force from a fluid reservoir (not shown) in fluid communication with the continuous fluid path 201, and driven along the continuous fluid path 201 to the mixing position 203. For the extracting purpose, a third driving signal that may be different from the first and second driving signal can be used.

Figure 8:
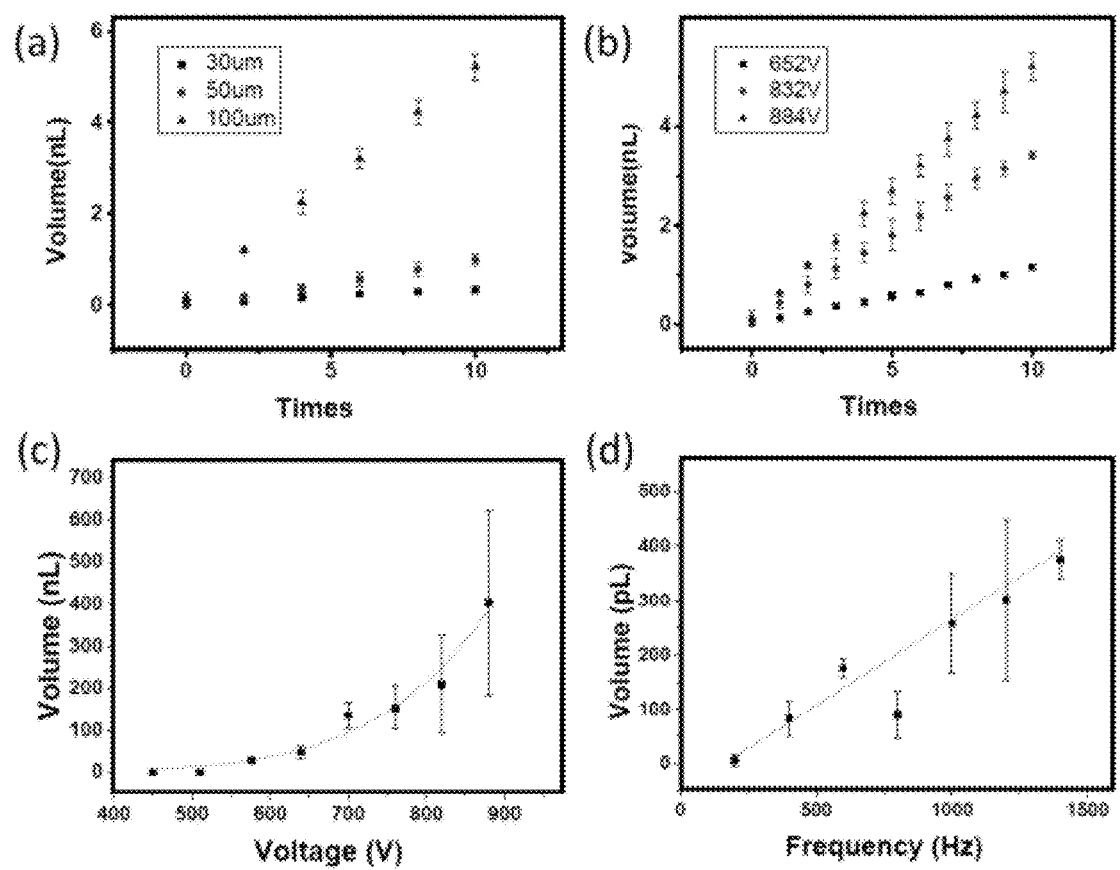
FIGS. 8(a) to 8(d) are diagrams illustrating the dependences of the jetted volume of a microfluidic drop on various factors using the method for on-chip microfluids dispensing according to certain embodiments of the present disclosure.

The method of the present disclosure allows jetting of a very small volume of microfluid out of a microfluidic drop, and mixing of the jetted volume into another microfluidic drop. In certain embodiments, the jetted volume is in the range of femtoliters, picoliters and nanoliters (i.e. between $10^{-15}$ and $10^{-12}$ liters, $10^{-12}$ and $10^{-9}$ liters, and between $10^{-9}$ and $10^{-6}$ liters). Dispensing of such a small volume is not possible with conventional micropipettes or other methods known in the art. A crucial aspect of the method discussed herein is the precise control of the volume of the first microfluidic drop 901 to be jetted to the mixing position 203. The present disclosure realizes the factors relevant to the jetted volume can include the magnitude (peak-to-peak voltage), frequency and duration of the second driving signal HV that is applied to the second electrode 103 and the width of the second electrode 103. The above factors can all be positively correlated to the jetted volume. FIGS. 8(a) to 8(d) are the results of a series of experiments illustrating the correlation, where a peak pulse second driving signal HV and an elongate rod shaped second electrode 103 are used. 100 uM DNA in 10 mM phosphate buffer solution was used for extracting the first microfluidic drop 901, but other types of solutions would work just as well. FIG. 8(a) shows the total jetted volume as a function of times of jetting operation duration of the second driving signal HV applied to the second electrode 103, given different widths (30 µm, 50 µm and 100 µm) of the second electrode 103. The second driving signal HV had a peak-to-peak voltage of 880V, a frequency of 800 Hz, and a duration of 2 seconds for each activation. The linear relationship suggests a very consistent jetted volume for various jetting operations in a single experiment setup. The experiments also show a larger width of the second electrode 103 leads to a larger jetted volume of the microfluidic drop. FIG. 8(b) shows the total jetted volume as a function of times of jetting operation, with the width of the second electrode 103 being 100 µm, and given different voltages (652V, 832V and 884V) of the second driving signal HV. Again the linear relationship suggests a very consistent jetted volume for various jetting operations in a single experiment setup. The experiments further show a larger voltage of the second driving signal HV leads to a larger jetted volume of the microfluidic drop. The experiments in FIG. 8(c) further reveal a quantitative characterization of the relationship of the jetted volume and the voltage of the second driving signal HV. The curve shows the jetted volume goes up quickly as the voltage of the second driving signal HV rises from 500V to 900V. Basically no ejection can be observed when the second driving signal is below 500V, while the jetted volume is less precise as the second driving signal HV goes beyond 750V. FIG. 8(d) further shows the jetted volume as a function of the frequency of the second driving signal HV applied to the second electrode 103, which is generally linearly proportional in the range of 200 Hz to 1,500 Hz.

With the apparatus, system and method of the present disclosure, it is possible to mix microfluids of a very small volume in the range of femtoliters, picoliters and nanoliters. Therefore, it is no longer necessary to mix two microfluidic samples of relatively large volumes and resort to complex fluid splitting operations afterwards. In addition, it is possible to mix two or more microfluidic samples of different volumes, whereas the traditional methods using EWOD force can only mix two microfluidic samples of the same volume. Because it is possible to quantify the jetting volume of a microfluidic drop based on a number of factors, the present disclosure is able to achieve dispensing and mixing of a very small volume of microfluid at a high precession. The system setup is significantly simplified compared with systems serving the same purpose in the art. The apparatus and system of the present disclosure further allows simultaneous operations to be carried out, thereby improving the efficiency.

Although the invention has been described in terms of certain embodiments, other embodiments apparent to those of ordinary skill in the art are also within the scope of this invention. Accordingly, the scope of the invention is intended to be defined only by the claims which follow.

What is claimed is:

1. A method for on-chip microfluids dispensing, comprising the steps of:
    (a) providing a plurality of first electrodes underlying a continuous fluid path for retaining microfluidic drops, the plurality of first electrodes are capable of generating an electro-wetting on dielectric (EWOD) force acting on the microfluidic drops and along the continuous fluid path;
    (b) providing a second electrode embedded within one or more of the plurality of first electrodes, the second electrode defines a jetting position on the continuous fluid path;
    (c) providing a first microfluidic drop at the jetting position;
    (d) applying a second driving signal via the second electrode to the first microfluidic drop, such that a controlled volume of the first microfluidic drop is jetted to a mixing position next to the jetting position on the continuous fluid path; and
    (e) providing a second microfluidic drop at the mixing position, such that the second microfluidic drop absorbs the controlled volume of the first microfluidic drop jetted to the mixing position.

2. The method of claim 1, wherein step (c) comprises loading the first microfluidic drop at a first loading position away from the jetting position and applying a first driving signal to the plurality of first electrodes to generate a EWOD force that drives the first microfluidic drop from the first loading position to the jetting position.

3. The method of claim 1, wherein step (e) comprises loading the second microfluidic drop at a second loading position away from the mixing position and applying a first driving signal to the plurality of first electrodes to generate a EWOD force that drives the second microfluidic drop from the second loading position to the mixing position.

4. The method of claim 3, wherein step (e) further comprises applying a first driving signal to the plurality of first electrodes to generate a EWOD force that drives the second microfluidic drop back and forth along the continuous fluid path at the mixing position.

5. The method of claim 2, wherein the first driving signal is an AC signal with a peak to peak voltage of 5 to 300 V and a frequency of 1-4 kHz.

6. The method of claim 1, wherein the second driving signal is an AC signal with a peak to peak voltage of 500 to 2,000 V and a frequency of 10 Hz to 2 kHz.

7. The method of claim 6, wherein the peak pulse signal is applied for 0.1 to 10 seconds for each jetting operation.

8. The method of claim 1, wherein the controlled volume of the first microfluidic drop is positively correlated to at least one of the following factors: the voltage of the second driving signal, the frequency of the second driving signal, the duration of the second driving signal and the width of the second electrode.

9. The method of claim 1, wherein the method is used for dispensing DNA solutions, protein solutions, organic solutions or inorganic salt solutions.

10. The method of claim 1, wherein the controlled volume of the first microfluidic drop is in the range of $10^{15}$ to $10'$ liters.

11. An apparatus for on-chip microfluids dispensing, comprising
    a bottom plate, the bottom plate comprises:
        a substrate;
        a plurality of first electrodes arranged one next to another on the substrate;
        a dielectric layer above and enclosing the plurality of first electrodes; and
        a second electrode on the substrate,
        wherein each of the plurality of first electrodes is in electric communication with a respective first driving signal input;
        wherein the second electrode is in electric communication with a second driving signal input;
        wherein the plurality of first electrodes define a continuous fluid path along a longitudinal direction for retaining microfluidic drops, and
        wherein the second electrode is arranged within the continuous fluid path and defines a jetting position and an adjacent mixing position within the continuous fluid path.

12. The apparatus of claim 11, wherein the second electrode has a width between 10 μm and 500 μm.

13. The apparatus of claim 11, wherein the second electrode is embedded within one or more adjacent first electrodes.

14. The apparatus of claim 13, wherein the one or more adjacent first electrodes comprise an elongate channel across the one or more adjacent first electrodes in the longitudinal direction, and the second electrode is arranged within the elongate channel.

15. The apparatus of claim 11, wherein the second electrode is stacked on one or more adjacent first electrodes and encapsulated by the dielectric layer.

16. The apparatus of claim 11, further comprising a hydrophobic layer on top of the dielectric layer.

17. The apparatus of claim 11, further comprising a plurality of fences on the plurality of first electrodes to prevent microfluidic drops from drifting away from the continuous fluid path.

18. The apparatus of claim 11, further comprising:
   a top plate; and
   a spacer between the top plate and the bottom plate,
      wherein the top plate, the bottom plate and the spacer define a cavity for retaining microfluidic drops.

19. The apparatus of claim 18, wherein the top plate comprises a conductive and grounded layer.

20. The apparatus of claim 11, wherein the apparatus comprises multiple independent continuous fluid paths.

21. A system for on-chip microfluids dispensing, comprising:
   an apparatus of claim 11,
   a control unit, comprising:
   an array of relays having a plurality of first driving signal outputs and a second driving signal output, each of the plurality of the first driving signal outputs is in electric communication with a respective first driving signal input of the apparatus, and the second driving signal output is in electric communication with the second driving signal input of the apparatus;
   a signal generator in electric communication with the array of relays, the signal generator generates a first driving signal and a second driving signal; and
   a controller in electric communication with the array of relays, the controller determines the outputs of the plurality of first driving signal outputs and the second driving signal output.

* * * * *